US006083911A

United States Patent [19]
Campbell et al.

[11] Patent Number: 6,083,911
[45] Date of Patent: Jul. 4, 2000

[54] ARENAVIRUS RECEPTOR AND METHODS OF USE

[75] Inventors: Kevin P. Campbell; Michael Henry; Hiroki Yamada; Roger Williamson, all of Iowa City, Iowa; Wei Cao, San Diego; Michael Oldstone, La Jolla, both of Calif.

[73] Assignee: University of Iowa Research Foundation, Iowa City, Iowa

[21] Appl. No.: 09/208,707

[22] Filed: Dec. 10, 1998

[51] Int. Cl.[7] .......................... A61K 35/34; A61K 38/16
[52] U.S. Cl. .................... 514/8; 514/8; 424/548
[58] Field of Search .............................. 514/8; 424/548; 435/240.2

[56] References Cited

U.S. PATENT DOCUMENTS 5,260,209  11/1993  Campbell et al. .................... 435/240.2

OTHER PUBLICATIONS

Borrow, P., and Oldstone, M., *J. Virol.* 66: 7270 (1992).
Williamson et al., *Hum. Mol. Genet.* 6: 831–41 (1997).
Igraghimov–Beskrovnaya et al., *Nature* 355: 696–702 (1992).
Yamada et al., *J. Neurochem.* 66: 1518–1524 (1996).
Mickelson et al., *Am. J. Physiol.* 267: C282–C292 (1994).
Fazakerley et al., *J. Gen. Virol.* 72: 1611–1625 (1991).
Mortensen et al., *Mol. and Cell Biol.* 12: 2391–5 (1992).

*Primary Examiner*—Russell Travers
*Attorney, Agent, or Firm*—Kevin M. Farrell

[57] ABSTRACT

Disclosed is a method for inhibiting the binding of an arenavirus to a cellular receptor. The method involves providing, in soluble form, a reagent comprising $\alpha$-dystroglycan or a portion thereof, the reagent being characterized by the ability to bind to the arenavirus thereby inhibiting the binding of the arenavirus to the cellular receptor. The reagent is contacted with an arenavirus particle prior to infection of a cell by the arenavirus particle. Also disclosed are methods for treating an arenavirus infection in a patient and preventing an arenavirus infection in an individual at risk. These methods involve providing a therapeutic composition comprising $\alpha$-dystroglycan or a portion thereof which is characterized by the ability to bind to arenaviruses, thereby inhibiting the binding of arenaviruses to a cellular receptor; and administering the composition to the patient or individual at risk. Arenaviruses to which the methods of the present invention apply include, without limitation, Lymphocyte Choriomeningitis Virus, Lassa fever virus, Mobala, and Oliveros. In another aspect, the disclosure relates to an embryonic stem cell line, and cells derived therefrom, which is homozygous for a disrupted dystroglycan gene, wherein the disruption prevents the synthesis of functional dystroglycan in the cells. Applications of the dystroglycan null embryonic stem cells include producing dystroglycan or a portion thereof in the cells and also for identifying portions of dystroglycan necessary for arenavirus infection. Also disclosed is a method for identifying antiviral compounds which interfere specifically with the binding of arenavirus and $\alpha$-dystroglycan, comprising providing a binding assay system for the determination of binding of arenavirus and $\alpha$-dystroglycan. The candidate antiviral compounds are introduced into the binding assay system and antiviral compounds which substantially inhibit binding of arenavirus to $\alpha$-dystroglycan are identified.

22 Claims, 3 Drawing Sheets

ARENAVIRUS RECEPTOR AND METHODS OF USE

BACKGROUND OF THE INVENTION

Certain arenaviruses are the causative agents of several severe and frequently fatal human hemorrhagic fevers. Among these pathogens, Lassa fever virus (LFV) produces high morbidity and mortality throughout West Africa. There are an estimated 250,000 persons infected by LFV per year, of whom 5,000 die. Lymphocytic choriomeningitis virus (LCMV) another arenavirus, can also cause human diseases, but has been studies primarily as the prototype of arenaviruses and a classical model of viral immunology and pathogenesis. Arenaviruses can cause a persistent infection in their rodent hosts, and humans who come in contact with excreted arenaviruses may become infected.

An understanding of the early events of arenavirus-host cell interaction, the viruses' tropism and pathogenesis, should facilitate the development of the strategies to block initial virus-cell interactions. For initiation of infection, the LCMV glycoprotein GP-1 on the surface of the virion likely anchors the virus to the cell surface via a proteinaceous receptor(s). Since LCMV infects a wide variety of cell types from many different mammalian hosts both in vitro and in vivo, this receptor is likely conserved and ubiquitously expressed. However, LCMV attaches poorly to lymphoid cells or cells adapted to grow in suspension, suggesting that the receptor may be involved in adhesion interactions.

Previously, a virus overlay protein blot assay (VOPBA) revealed a single high molecular weight glycoprotein that specifically bound to purified LCMV (P. Borrow and M. Oldstone, *J. Virol.* 66: 7270 (1992)). This molecule was identified as a glycoprotein sensitive to a battery of proteases, glycosidases and tunicamycin (P. Borrow and M. Oldstone, *J. Virol.* 66: 7270 (1992)).

SUMMARY OF THE INVENTION

In one aspect the present invention relates to a method for inhibiting the binding of an arenavirus to a cellular receptor. The method involves providing, in soluble form, a reagent comprising α-dystroglycan or a portion thereof, the reagent being characterized by the ability to bind to the arenavirus thereby inhibiting the binding of the arenavirus to the cellular receptor. The reagent is contacted with an arenavirus particle prior to infection of a cell by the arenavirus particle. Also encompassed within the scope of the invention are methods for treating an arenavirus infection in a patient and preventing an arenavirus infection in an individual at risk. These methods involve providing a therapeutic composition comprising α-dystroglycan or a portion thereof which is characterized by the ability to bind to arenaviruses, thereby inhibiting the binding of arenaviruses to a cellular receptor; and administering the composition to the patient or individual at risk. Arenaviruses to which the methods of the present invention apply include, without limitation, Lymphocyte Choriomeningitis Virus, Lassa fever virus, Mobala, and Oliveros.

Another aspect of the invention is an embryonic stem cell line, and cells derived therefrom, which is homozygous for a disrupted dystroglycan gene, wherein the disruption prevents the synthesis of functional dystroglycan in the cells. Such cells are useful for producing dystroglycan or a portion thereof in dystroglycan null embryonic stem cells and also for identifying portions of dystroglycan necessary for arenavirus infection.

In another embodiment, the invention relates to a method for identifying antiviral compounds which interfere specifically with the binding of arenavirus and α-dystroglycan, comprising providing a binding assay system for the determination of binding of arenavirus and α-dystroglycan. The candidate antiviral compounds are introduced into the binding assay system and antiviral compounds which substantially inhibit binding of arenavirus to α-dystroglycan are identified. A useful assay system for this method is a dystroglycan null embryonic stem cell line which contains introduced α-dystroglycan or a portion thereof necessary for arenavirus binding.

DETAILED DESCRIPTION OF THE INVENTION

Figure 1:
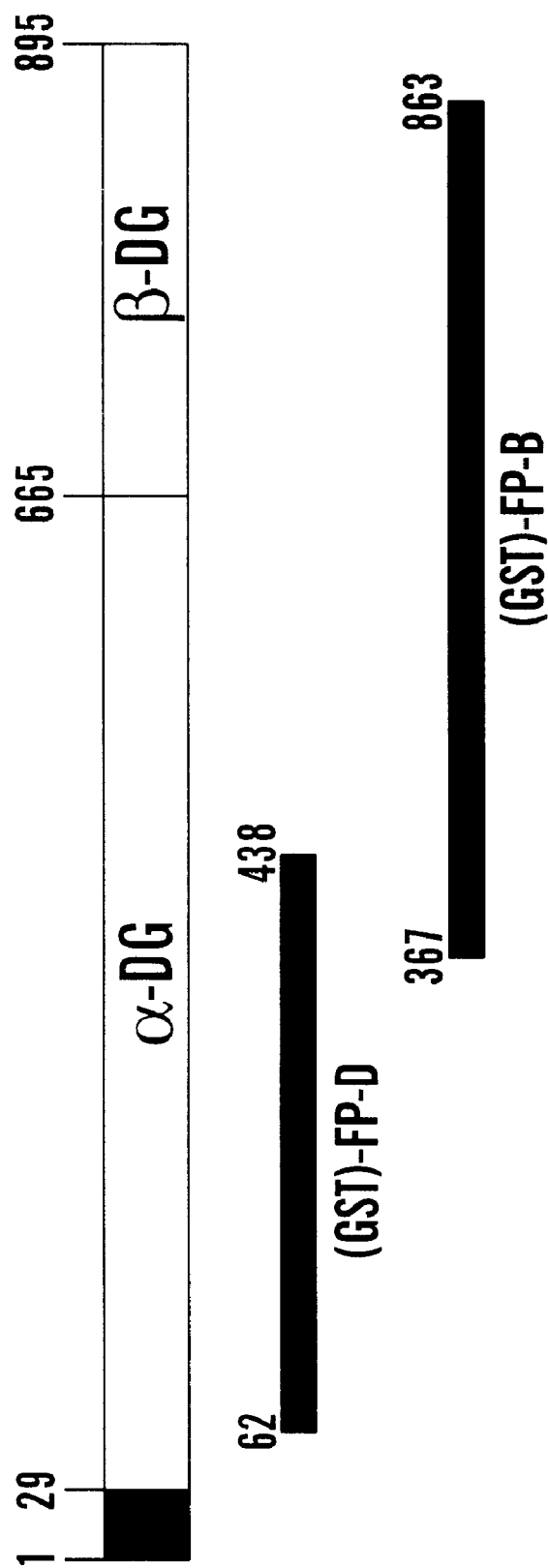
FIG. 1 is a schematic diagram showing dystroglycan precursor and GST-fusion proteins. Signal sequence (residues 1–28) is shown in solid box. The sequence corresponding to α-DG (residues 29–653) and β-DG (residues 654–895) are shown as open boxes. Fusion protein GST-FP-D contains residues 62–438 of the dystroglycan precursor. Fusion protein GST-FP-B contains residues 367–863 of the dystroglycan precursor.

The present invention is based on the discovery that α-dystroglycan is a common cellular receptor for lymphocytic choriomeningitis virus (LCMV), Lassa fever virus (LFV) and other arenaviruses. Dystroglycan is encoded by a single gene, and processed into two mature proteins α- and β-dystroglycan, which form a protein complex on the cell surface. Nucleotide sequences which encode dystroglycan are described by Campbell et al., U.S. Pat. No. 5,260,209 (1993), the contents of which are herein incorporated by reference. The present invention provides methods for inhibiting the binding of an arenavirus to a cellular receptor by competitively inhibiting arenavirus particle binding to a receptor by first binding with soluble α-dystroglycan or a portion thereof which binds the arenavirus. The method comprises contacting the arenavirus particle with a soluble form of a reagent comprising α-dystroglycan or a portion thereof, which has the ability to bind to the arenavirus and thereby inhibit the binding of the arenavirus to the cellular receptor.

As detailed in the Exemplification section of this application, soluble native α-dystroglycan competes for virus binding to cell surface virus receptors in a dose-dependent manner. At the appropriate concentration, α-dystroglycan effectively blocks infectivity and reduces production of progeny virus of arenaviruses which utilize α-dystroglycan as a cellular receptor. Experiments detailed in the Exemplification indicate that arenaviruses do not bind a fragment of α-dystroglycan lacking the extreme amino-terminus which was produced in bacteria, but do bind full length α-dystroglycan produced in mammalian cells. This indicates that the extreme amino-terminus of α-dystroglycan and/or post-translational modifications to this protein which occur in mammalian cells are crucial for LCMV recognition. Therefore the α-dystroglycan or portion thereof in the reagent of the above method must contain any regions and/or post-translational modifications required for arenavirus binding to effectively inhibit arenavirus binding to the cellular receptor.

To be effective, the reagent must be contacted with the arenavirus under conditions appropriate for virus binding. Contact with the arenavirus particle must be made prior to infection of the cell by the particle, in order to prevent binding to the receptor of that cell. The method of contacting the reagent to the arenavirus particle depends upon the circumstances with which the method is employed, and are discussed below.

Applications of the above method include both in vitro and in vivo situations. Examples of in vitro situations include cell culture and organ culture. In vitro applications include experimentation (e.g. the study of viral pathology) or alternatively the prevention or elimination of arenavirus infection of cells or tissue. Suitable routes of contacting the virus with the reagent in vitro include adding the reagent to cell culture medium, or injecting the reagent into tissue.

Examples of in vivo applications of the above methods include therapies for treating an arenavirus infection in a patient, and also the prevention of infection of an individual at risk for arenavirus infection. The reagent may be contacted to the virus present or suspected of being present in a patient via a physiologically acceptable carrier.

As detailed in the Exemplification section soluble α-dystroglycan competes for virus binding to cell surface virus receptors in a dose-dependent manner. At the appropriate concentration, soluble α-dystroglycan effectively blocks infectivity and reduces production of progeny virus of arenaviruses which utilize α-dystroglycan as a cellular receptor. These arenaviruses include both Old World and New World arenaviruses, including, but not limited to several strains of LCMV (e.g. C1 13, Armstrong 5, and WE54), LFV, Mobala, Oliveros, specifically bind native α-dystroglycan. The above method is not expected to inhibit binding of an arenavirus which does not bind α-dystroglycan, such as Guanarito.

Another aspect of the present invention is the therapeutic method for treating an arenavirus infection in a patient. The method comprises providing a therapeutic composition comprising α-dystroglycan or a portion thereof which is characterized by the ability to bind to arenaviruses. As described above, the α-dystroglycan or portion thereof used in the method must be either native or otherwise of a form suitable for virus binding, including any post-translational modifications of native α-dystroglycan necessary for virus binding, in order to enable sufficient binding to an arenavirus to inhibit arenavirus binding to the cellular receptor.

The therapeutic composition is administered to the patient in a sufficient amount to produce a therapeutic effect. The preferred route of administration depends upon the particular infection. In a preferred embodiment, administration is intravenous. The patient is any mammal which is afflicted with an appropriate arenavirus infection. In a preferred embodiment, the patient is human. This therapeutic method is suitable for treatment of any infection which arises from an arenavirus which is characterized as binding α-dystroglycan, described above.

Another aspect of the present invention is the prevention of arenavirus infection in an individual at risk. This method is similar to the method of treating an arenavirus infection, described above. The method comprises providing a composition comprising α-dystroglycan or a portion thereof which is characterized by the ability to bind to arenaviruses, described above, thereby inhibiting the binding of arenaviruses to a cellular receptor. Once provided, the composition is administered to the individual at risk. An individual at risk for arenavirus infection is an individual who is exposed to infectious arenavirus (e.g. by way of contact with an infected individual) or who is inordinately susceptible to arenavirus infection or the effects of a successful infection (e.g. an immunocompromized patient or a developing fetus). In a preferred embodiment, administration is intravenous. The composition may be administered to the individual at risk via a physiologically acceptable carrier.

The above methods of 1) treating an arenavirus infection in a patient, and 2) preventing an arenavirus infection in an individual at risk, also find application in the therapeutic treatment or prevention of an arenavirus infection of a developing fetus. LCMV infection of a developing fetus has been linked to developmental abnormalities. Administration of the compositions or reagents employed in the above described methods, to a developing fetus can be accomplished by either direct administration or alternatively by administration to the mother of the fetus.

Experiments detailed in the Exemplification section of this application investigate the function of dystroglycan, a cell-surface laminin receptor expressed by cells contacting basement membranes in developing and adult tissues. Basement membranes are composed of ordered arrays of characteristic extracellular matrix proteins, but little is known about the assembly of these structures in vivo. In previous experiments, the dystroglycan gene was disrupted in the mouse (Williamson et al., *Hum. Mol. Genet.* 6: 831–41 (1997)). Dystroglycan null (DG–/–) embryos resulting from these experiments failed to progress beyond the early egg cylinder stage of development and were characterized by structural and functional perturbations of Reichert's membrane, one of the earliest basement membranes that form in the rodent embryo. These data indicated that dystroglycan is necessary for the development of Reichert's membrane and suggested that it might generally be important for the assembly of basement membranes.

Another aspect of the present invention is an embryonic stem (ES) cell line and cells derived therefrom, which is homozygous for a disrupted dystroglycan gene (DG–/– ES cells otherwise known as dystroglycan null ES cells) wherein the disruption prevents the synthesis of functional dystroglycan in the cells. The experiments presented in the Exemplification further characterize the function of dystroglycan using these DG–/– ES cells. In the preferred embodiment, the disruption of each dystroglycan gene comprises a deletion of a region of 5495 base pairs, which includes 3509 base pairs of the intronic sequences 5' to exon 2 and 1986 base pairs of the 5' portion of exon 2, and replacement of the deleted region with a gene cassette as a marker for drug resistance. As detailed in the Exemplification, this can be accomplished by generating the DG–/– ES cells from pre-existing ES cells which have a single dystroglycan gene disrupted by the insertion of a selection marker for neomycin resistance (DG+/– ES cells) (Williamson et al., *Hum. Mol. Genet.* 6: 831–41 (1997)) by at least two approaches. The first approach is to expose the DG+/– ES cells to high concentrations of neomycin to select for cells which lose the remaining wild-type allele as a result of chromosome loss duplication. This results in cells which have two identical copies of the dystroglycan gene (identically disrupted, with both disruptions containing a neomycin resistance selection marker).

The second approach, is to retarget the DG+/− ES cells with a second gene disruption construct which contains a selection marker other than neomycin. In a preferred embodiment, the gene disruption construct is identical to that used to generate the DG+/− cells (Williamson et al., Hum. Mol. Genet. 6: 831–41 (1997)), with the exception that the selection marker is for hygromycin resistance (Mortensen et al, Proc. Natl. Acad. Sci. USA 88: 7036–40 (1991)). This results in cells which have two copies of the dystroglycan gene, both disrupted in the positions described above, with one disruption containing a neomycin resistance selection marker, and the other disruption containing a hygromycin resistance selection marker.

As detailed in the Exemplification section which follows, the DG−/− cells were used to generate DG−/− embryoid bodies. Results of these experiments indicate that dystroglycan is required for the formation of a basement membrane in embryoid bodies and further indicate that dystroglycan-laminin interactions are pre-requisite for the deposition of other basement membrane proteins. Dystroglycan may exert its influence on basement membrane assembly by binding soluble laminin and organizing it on the cell surface. These data establish a role for dystroglycan in the assembly of basement membranes and indicate fundamental mechanisms underlying this process.

Another aspect of the present invention is a method for producing dystroglycan or a portion of dystroglycan from cells in culture, specifically from dystroglycan null ES cells. The method comprises introducing an adenovirus expression vector containing nucleotide sequence which encode dystroglycan to the dystroglycan null ES cells under conditions appropriate for expression. The dystroglycan or portion thereof which is produced is then purified from the cells by conventional methods (e.g. immunopurification). Experiments detailed in the Exemplification indicate that introduction of an adenovirus expression vector containing sequences encoding dystroglycan or a portion thereof, under conditions appropriate for expression, results in the production of dystroglycan or a portion thereof by the recipient cells.

$\alpha$-dystroglycan and $\beta$-dystroglycan, are processed from a precursor dystroglycan protein which is transcribed from the dystroglycan gene Dagl (GenBank Accession #U48854). Expression of nucleotide sequences encoding dystroglycan results in the production of both $\alpha$- and $\beta$-dystroglycan proteins. Sequences encoding wild type species of dystroglycan can be used in the above method to produce native $\alpha$- and $\beta$-dystroglycan. Alternatively, dystroglycan nucleotide sequences containing truncations, internal deletions, or point mutations can be used to produce altered species of dystroglycan, having altered forms of either, or both, $\alpha$- and $\beta$-dystroglycan. Altered forms of $\alpha$- and $\beta$-dystroglycan include proteins with N-terminal or C-terminal truncations, internal deletions, or amino acid substitutions. The deletion or mutation of any dystroglycan amino acid residues which are necessary for post-translational modifications (e.g. glycosylation) present on the native $\alpha$- and $\beta$-dystroglycan proteins will result in producing dystroglycan proteins with altered or absent post-translational modifications. Such mutant proteins are useful in studying the role that specific post-translational modifications play in protein function and virus infection.

Protein obtained from the above method can be used for several purposes including, but not limited to, experimental analysis of arenavirus binding. Dystroglycan or a portion thereof which is determined to be involved in or necessary for arenavirus binding and/or infectivity can be used for such purposes as 1) therapeutic administration to a patient for treatment of arenavirus infection, 2) administration to an individual at risk to prevent arenavirus infection, 3) development of a vaccine against arenavirus infection. One benefit to producing such proteins in DG−/− ES cells, rather than in prokaryotic cells, is the ability of the ES cells to perform any post-translational modifications of the dystroglycan protein necessary for function or virus infection.

Another aspect of the present invention is a method for high efficiency gene transfer of a nucleotide sequence into ES cells. Experiments detailed in the Exemplification indicate that an adenovirus expression vector containing a nucleotide sequence introduced into ES cells under conditions appropriate for expression, results in the expression of the nucleotide sequences in a high percentage of recipient ES cells. In a preferred embodiment the ES cells are DG null cells. In another preferred embodiment, the adenovirus expression vector contains nucleotide sequences which encode dystroglycan or a portion thereof, described above. The dystroglycan or portion thereof can be either wild type or an altered version, as described above.

The present invention can also be used for identifying portions of dystroglycan necessary for arenavirus infection. An adenovirus expression vector which encodes a mutated dystroglycan in which a particular portion of the wild type molecule is either absent or modified, is introduced into DG null ES cells under conditions appropriate for the expression of the mutated dystroglycan. The cells produced are then assayed for susceptibility to arenavirus infection. Expression of mutated dystroglycan which lacks a functional portion of dystroglycan necessary for arenavirus infection is not expected to confer virus susceptibility to recipient DG null ES cells. Alternatively, mutated dystroglycan which lacks a portion of dystroglycan which is unnecessary for arenavirus infection will still confer susceptibility. Although $\alpha$-dystroglycan is sufficient, it is likely that at least portions of both $\alpha$- and $\beta$- are necessary for arenavirus infection. By comparing different mutants of dystroglycan for their ability to confer arenavirus susceptibility, one can determine which portion or portions of dystroglycan (both $\alpha$- and $\beta$-) are necessary for arenavirus infection. Various arenaviruses can be used in this method, to determine if the different arenaviruses utilize the same portions of dystroglycan for infection.

A similar method to that described directly above can be utilized to determine which portion of $\alpha$-dystroglycan is sufficient for arenavirus binding. DG null ES cells to which only a portion of $\alpha$-dystroglycan has been introduced (e.g. by genetic engineering) under conditions appropriate for arenavirus binding, can be assayed for arenavirus binding to determine if the portion of $\alpha$-dystroglycan expressed is sufficient. In one embodiment, arenavirus binding is assayed by determining infectivity of an arenavirus towards the produced cells. In a preferred embodiment, the portion of $\alpha$-dystroglycan to be tested is introduced by genetic engineering as a nucleic acid sequence encoding dystroglycan precursor in which amino acid sequences corresponding to $\alpha$-dystroglycan are replaced with amino acid sequences corresponding to the appropriate portion of $\alpha$-dystroglycan, under conditions appropriate for expression. This can be successfully accomplished using an adenovirus expression vector, as described above. Various arenaviruses which are known to bind to $\alpha$-dystroglycan, described above, can be used in this method, to determine if the different arenaviruses utilize the same portions of $\alpha$-dystroglycan for binding.

Another aspect of the present invention is a method for identifying antiviral compounds which interfere specifically with the binding of arenaviruses and α-dystroglycan. This method utilizes a binding assay system for the determination of binding of arenavirus and α-dystroglycan. Suitable binding assay systems are available and within the means of one of average skill in the art. In a preferred embodiment, the binding assay is a cell assay system. In one embodiment, the cell assay system utilizes cells which are susceptible to arenavirus infection via α-dystroglycan binding. In such a system, binding can be assayed by determining infectivity of the virus towards the cells. One example of such an assay system is a DG null ES cell line which contains introduced α-dystroglycan or a portion thereof necessary for arenavirus binding, described above.

Once an assay system is in place, candidate antiviral compounds are introduced into the binding assay system and the effects of the compounds on arenavirus-α-dystroglycan binding is determined. Compounds which substantially inhibit binding are identified as antiviral compounds. Such compounds may have value as a vaccine component, and should be further analyzed for this potential. The possibility exists that different arenaviruses (e.g. LCMV, Mobala, Oliveros) exhibit different binding properties towards α-dystroglycan (e.g. bind to different portions of α-dystroglycan). Antiviral compounds which act specifically on one or more arenavirus species can be identified by using different arenaviruses or species in this assay.

EXAMPLIFICATION
Identification of α-dystroglycan as a Receptor for LCMV, LFV, and Other Arenaviruses.

Arenaviruses consist of several causative agents of fatal human hemorrhagic fevers (Peters et al., in *Fields Virology* B. Fields, Ed. (Lippincott-Raven Publishers, Philadelphia, 1996), vol. 2, pp. 1521; A. Fabiyi, *Bull Pan Am Health Organ* 10: 335 (1976); Salas et al., *Lancet* 338: 1033 (1991)). Among these pathogens, Lassa fever virus (LFV) causes an estimated 250,000 cases and over 5,000 deaths annually (Peters et al., in *Fields Virology* B. Fields, Ed. (Lippincott-Raven Publishers, Philadelphia, 1996), vol. 2, pp. 1521; Frame et al., *Am. J. Trop. Med. Hyg.* 19: 670 (1970); McCormick et al., *J. Infect. Dis.* 155: 437 (1987)). Lymphocytic choriomeningitis virus (LCMV), the prototype arenavirus, has been studied primarily in its natural rodent host as a model of viral immunology and pathogenesis (P. Borrow and M. B. A. Oldstone, in *Viral Pathogenesis* N. Nathanson, Ed. (Lippincott-Raven Publishers, Philadelphia, 1997) pp. 593; R. M. Zinkernagel, *Science* 271: 173 (1996); R. M. Zinkernagel, *Scand. J. Immunol.* 46: 421 (1997); Oldstone et al., *Prog. Med. Virol.* 26: 45 (1980); Rowe, *Rev. Rep. Naval. Med. Res. Inst.* 12: 167 (1954)).

To initiate infection, the LCMV glycoprotein GP-1 anchors the virus to the cell surface via a proteinaceous receptor (P. Borrow and M. Oldstone, *J. Virol.* 66: 7270 (1992); J. Burns and M. Buchmeier, *Virology* 183: 620 (1991)), which by a virus overlay protein blot assay (VOPBA) has been identified as a single high molecular weight glycoprotein (P. Borrow and M. Oldstone, *J. Virol.* 66: 7270 (1992)). The presence of the receptor protein correlated directly with a cell's susceptibility to LCMV attachment and infection. Its broad migration pattern on SDS-PAGE is likely to reflect the heterogeneity in cell-type specific post-translational modifications (P. Borrow and M. Oldstone, *J. Virol.* 66: 7270 (1992)). In addition to murine cells, a broad range of rodent and primate cells express the same protein (P. Borrow and M. Oldstone, *J. Virol.* 66: 7270 (1992)). LFV bound to what appears to be the same glycoprotein, suggesting that both viruses may share a common cellular receptor.

Purification of this putative receptor protein was done from a LCMV permissive cell line by sequential column chromatography and a total of five tryptic peptides were sequenced. Peptides GT384, GT441 and GT417 showed complete homology to dystroglycan (DG) precursor protein at regions of aa 610–623, 571–585, 516–533, respectively.

Dystroglycan is encoded by a single gene, and processed into two mature proteins α- and β-dystroglycan (α-DG and β-DG), which form a complex spanning the plasma membrane (Ibraghimov-Beskrovnaya et al., *Nature* 355: 696 (1992)). The sequences corresponding to the three peptides are near the carboxyl terminus of α-DG. α-DG is an extracellular peripheral membrane protein that binds to the extracellular matrix and is non-covalently associated with α-DG which is a transmembrane protein linked to the cytoskeleton (M. Henry and K. Campbell, *Curr. Opin. Cell Biol.* 8: 625 (1996)). dystroglycan complex is expressed in a wide variety of tissues and cells, and plays an important role in mediating cell-extracellular matrix interactions (Durbeej et al., *J. Histochem. Cytochem.* 46: 449 (1998); Williamson, et al., *Hum. Mol. Genet.* 6: 831 (1997)). The putative LCMV receptor was preferentially expressed on the basolateral surface of polarized MDCK cells, facilitating a basolateral route of LCMV entry (Borrow et al., submitted (1998)), paralleling a similar localization of dystroglycan expression (Durbeej et al., *J. Histochem. Cytochem.* 46: 449 (1998)).

The interaction between α-DG and LCMV was demonstrated in VOPBAs with several strains of LCMV (Cl 13, Armstrong 5 (Arm5) and WE54) on blots containing purified α-DG proteins. All these LCMV strains bound to purified native α-DG protein (Yamada, et al., *J. Neurochem.* 66: 1518 (1996)). In contrast, none of these viruses recognized the *E. coli*-expressed glutathione S-transferase (GST)-fusion proteins with either FP-D or FP-B, which encoded different regions of dystroglycan precursor sequence (Ibraghimov-Beskrovnaya, et al., *Nature* 355: 696 (1992)) (FIG. 1), suggesting that the extreme amino-terminus of α-DG and possibly, post-translational modifications on this protein are crucial for LCMV recognition. A similarly purified glycoprotein, α2 subunit of dihydropyridine receptor complex (purified from rabbit skeletal muscle as described in Mickelson et al., *Am. J. Physiol.* 267: C282 (1994)), also negatively charged through glycosylation, did not bind to LCMV. Like LCMV, the arenaviruses LFV, Mobala and Oliveros bound to purified native α-DG protein, but not to the recombinant GST-FP-D or GST-FP-B proteins. In contrast, the arenavirus Guanarito failed to recognize α-DG protein.

Figure 2B:
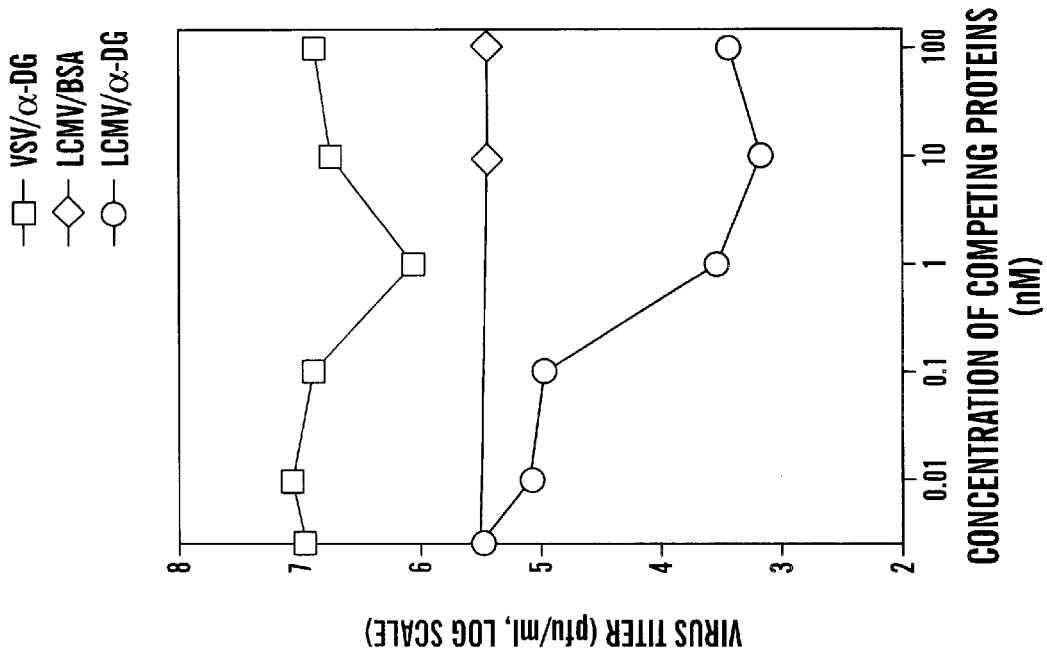
FIG. 2 is a diagrammatic representation of data from experiments in which LCMV infection was blocked with soluble α-dystroglycan protein. A) The number of cells infected in the present of increasing concentrations of competing proteins. B) Virus titers ($\log_{10}$ pfu/ml) are plotted against the concentration of competing proteins added during absorption.
Figure 2A:
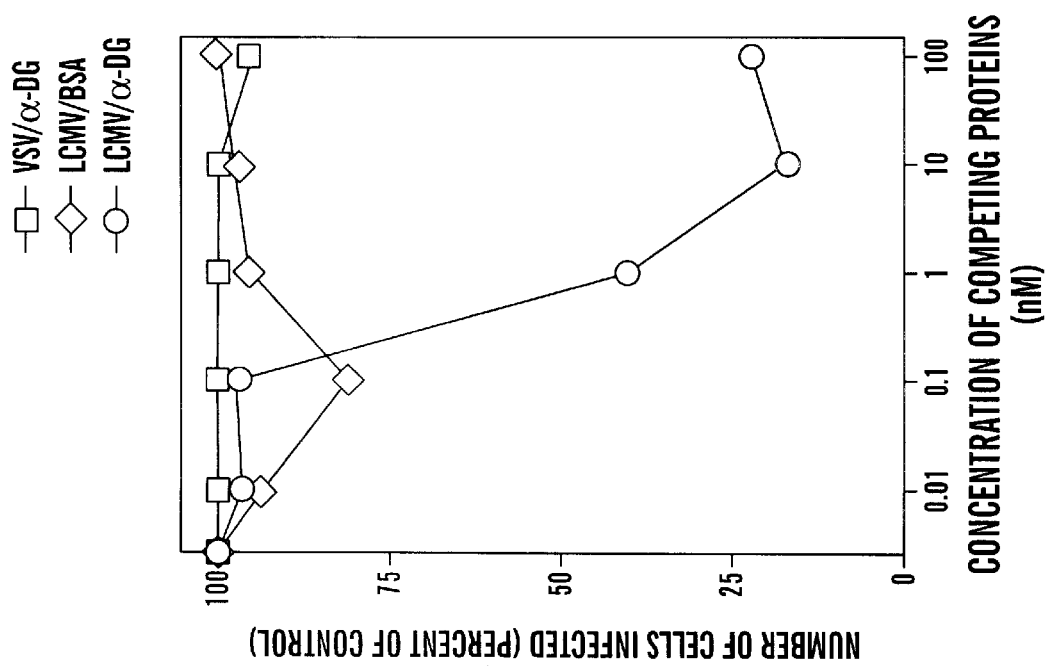

Purified soluble α-DG competed with the cell surface virus receptor during LCMV infections in a dose-dependent manner (FIG. 2). α-DG at 0.9 nM concentration effectively blocked LCMV infectivity (FIG. 2A), and significantly reduced production of progeny LCMV (FIG. 2 B). Soluble α-DG blocked infection by LFV at similar concentrations, but roughly 100-fold higher amounts were required to block LCMV Arm5 infectivity (Cao et al., unpublished results). In contrast, α-DG had no effect on the infection by an unrelated RNA virus Vesicular Stomatitis virus (VSV) (FIG. 2B).

A mouse embryonic stem (ES) cell line expressing dystroglycan (wt) was readily infected by LCMV (at MOI of 10, >90% of cells were infected). However, LCMV replication did not occur in dystroglycan null ES (ko) cells, described below, (at MOI of 10, <0.1% of cells were infected), yet these cells were viable, maintained a growth rate similar to the parental cells and were equally infectable by VSV. When the α-DG protein was restored on the surface of ko cells by infection with an adenovirus vector carrying dystroglycan cDNA, these cells again became susceptible to LCMV infection (at MOI of 10, about 75% of cells were infected). However, when the same adenovirus vector expressing GFP or lacZ was used for infection, less than 0.1% ko cells were infectable by LCMV.

Old World arenaviruses including LCMV, LFV and Mobala, which are phylogenetically and serologically distinct from the New World arenaviruses (Peters et al., in *Fields Virology* B. Fields, Ed. (Lippincott-Raven Publishers, Philadelphia, 1996), vol. 2, pp. 1521; J. Clegg, in *The Arenaviridae* M. Salvato, Ed. (Plenum, New York, 1993) pp. 175), specifically recognized the α-DG receptor protein. Interestingly, Oliveros virus, a group C New World arenavirus (Peters et al., in *Fields Virology* B. Fields, Ed. (Lippincott-Raven Publishers, Philadelphia, 1996), vol. 2, pp. 1521; Bowen et al., *Virology* 219: 285 (1996)), also bound to α-DG in VOPBA but Guanarito, another New World Arenavirus, failed to do so. Usage of ES ko cells alone and reconstituted with dystroglycan will be of great value to further group the arenaviruses.

Cellular receptors are key elements in determining the tropism and pathogenesis of virus infection. The presence of α-DG in all the tissues and organs examined to date correlates with the tropism of LCMV (P. Borrow and M. Oldstone, *J. Virol.* 66: 7270 (1992); Fazakerley et al., *J. Gen. Virol.* 72: 1611 (1991)). High sequence conservation in the dystroglycan gene (M. Henry and K. Campbell, *Curr. Opin. Cell Biol.* 8: 625 (1996)) supports the broad host range for LCMV and arenavirus infections of animals and humans (Peters et al., in *Fields Virology* B. Fields, Ed. (Lippincott-Raven Publishers, Philadelphia, 1996), vol. 2, pp. 1521). Characterization of the α-DG/arenavirus interaction should elucidate the early events of arenavirus infection and facilitate the development of strategies to intervene and prevent this crucial interaction.

Generation of Dystroglycan-Null Embryonic Stem Cells and Embryoid Bodies.

Figure 3:
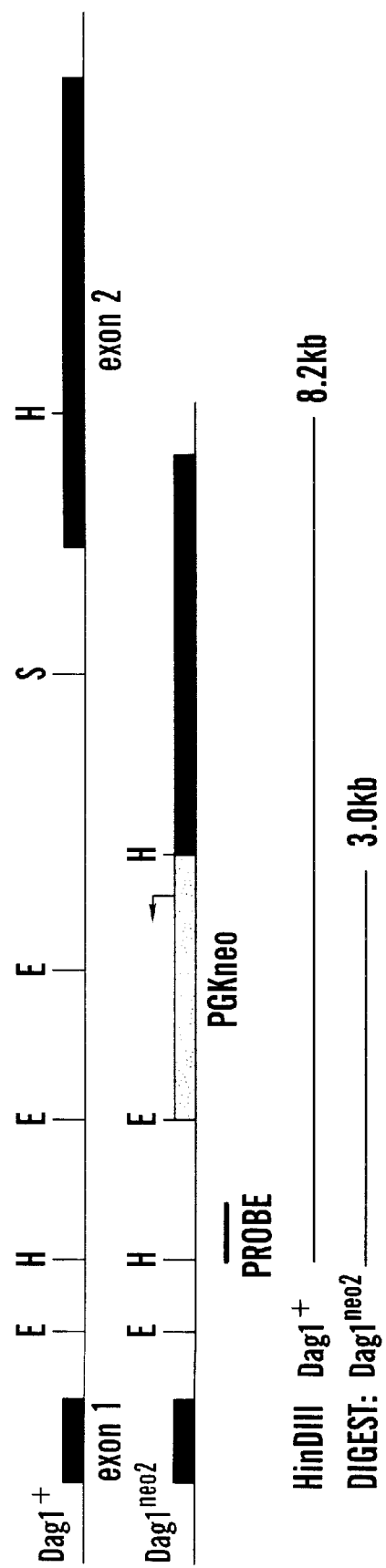
FIG. 3 is a schematic map of the wild-type ($Dag1^{\pm}$) and DG-null mutant ($DAG1^{null}$) alleles and the predicted fragment sizes from each after HindIII digestion. E=EcoRI; H=HindIII; S=SalI.

In an effort to explore further the biological role of dystroglycan, DG-null (DG–/–) ES cells were generated from existing heterozygous (DG+/–) ES clones (Williamson et al., *Hum. Mol. Genet.* 6: 831–41 (1997)). FIG. 3 shows the gene disruption strategy of mutant ES cell lines. Southern blot analysis of HindIII-digested DNA from wild-type, heterozygous (+/–), and homozygous-null (–/–) mutant ES cell lines showed a loss of the 8.2 kb wild-type fragment in the DG–/– cells. Despite the fact that dystroglycan is expressed in ES cells, no overt differences in the growth characteristics or cell morphology of undifferentiated DG–/– ES cell lines were observed.

Embryoid bodies were generated from DG–/– and control ES cell lines. The expression of dystroglycan was investigated using western blot analysis of embryoid body extracts and also immunoprobing of embryoid body sections, probing for β-dystroglycan. Both analyses showed that dystroglycan was expressed by the outer layer of endoderm and in cardiomyocytes that develop within the core of the control embryoid bodies, but, as expected, was not expressed in DG–/– embryoid bodies. DG–/– ES cells generated embryoid bodies that possessed several characteristic features including an outer layer of differentiated endoderm and spontaneously contracting cardiomyocytes in their core (Doetschman et al., *J. Embryol Exp. Morphol.* 87: 27–45 (1985)). The overall growth characteristics of DG–/– embryoid bodies were similar to wild-type and DG+/– controls. The gross morphology and histology of DG–/– embryoid bodies was essentially indistinguishable from controls, as examined by Hoffman modulated contrast imagery of 10 day old embryoid bodies, and also. Periodic acid-Schiff staining of sections from cystic 10-day-old embryoid bodies showed a similar proportion (~1%) of control and DG–/– embryoid bodies formed large fluid-filled cysts, consistent with the presence of differentiated visceral endoderm. Occasionally, the endodermal layer was separated from the underlying cells. Although this was observed in embryoid bodies regardless of genotype, it was noted more frequently in DG–/– embryoid bodies. Finally, DG–/– embryoid bodies generated spontaneously contracting cardiomyocytes, visually apparent as rhythmically beating embryoid bodies, in comparable proportions (~30%) and kinetics (by 8 days in culture) as wild-type and DG+/– controls. Consistent with these observations, molecular markers for endoderm and cardiomyocytes were detected by immunofluorescence analysis in both control and DG–/– embryoid bodies. Therefore DG–/– ES cells are able to generate embryoid bodies containing functionally differentiated endoderm and cardiomyocytes, the two cell types in which dystroglycan is expressed in embryoid bodies.

Basement Membrane Disruption in Dystroglycan-Null Embryoid Bodies.

Although certain aspects of embryoid body development appeared normal without dystroglycan expression, because of previous results with DG–/– mutant mouse embryos, a closer look was taken at the elaboration of a particular basement membrane in the mutant embryoid bodies. Typically, embryoid bodies develop a basement membrane subjacent to the outer layer of endoderm (Doetschman et al., *J. Embryol Exp. Morphol.* 87: 27–45 (1985); Martin et al., *Dev. Biol.* 61: 230–44 (1977)). Well-formed endodermal layers comprise a morphologically distinct feature of embryoid bodies in cross section. The sub-endodermal basement membrane in DG–/– and control embryoid bodies were examined by immunostaining cross sections with antibodies directed against various basement membrane proteins. In control embryoid bodies (wild-type and DG+/–) laminin α1 is co-localized with dystroglycan on the basal surfaces of endodermal cells, showing a typical sheet-like basement membrane pattern. Other laminin al immunoreactivity was detected in the core of the embryoid bodies as small, irregular patches, appearing inside and outside of cells, but dystroglycan was not co-localized with this patchy laminin staining except where it overlapped with cardiomyocytes. In marked contrast, the sub-endodermal basement membrane staining pattern of laminin al was grossly disrupted in DG–/– embryoid bodies, instead only appearing as the patchy deposits described above. In a minority of dystroglycan –/– embryoid bodies, sub-endodermal staining of laminin α1 similar to that of control cultures was detected, however the ultrastructural analysis described below indicates that this is not organized into a basement membrane structure. Similar results were obtained using antisera reacting with the laminin β1 and γ1 chains, arguing that the laminin α1-specific antibody detected the entire laminin-1 heterotrimer. Interestingly, the disruption of basement membrane molecules in DG–/– embryoid bodies extended beyond dystroglycan's direct binding partner laminin-1. In wild-type and DG+/– embryoid bodies, type IV collagen and perlecan localized to the sub-endodermal basement membrane and patchy deposits in the cores like laminin-1, as detected by immunofluorescence analysis of 10 day old embryoid body sections. Similarly, the sub-endodermal basement membrane localization of these molecules was disrupted in DG–/– embryoid bodies. Western blot analysis was performed to confirm the immunofluorescence data and demonstrate that failed basement membrane formation in DG−/− embryoid bodies was not a secondary consequence of a lack of expression of laminin-1. This demonstrated that the laminin α1 is expressed in DG−/− embryoid bodies. The laminin α1 expression levels in the DG+/− and DG−/− embryoid bodies were lower than the wild-type control, but comparable to each other. The basis for this difference in laminin expression between wild-type and derivative embryoid bodies is not yet understood. However, despite the difference in the steady-state level of laminin α1 expression, DG+/− embryoid bodies elaborate well-defined sub-endodermal basement membranes similar to wild-type embryoid bodies. Since DG+/− and DG−/− embryoid bodies exhibited comparable levels of laminin α1, the failure of basement membrane formation in DG−/− embryoid bodies cannot be accounted for by reduced expression of laminin α1. Together, these results show that DG−/− embryoid bodies have a gross disruption in the localization pattern of several important basement membrane structural proteins.

To examine this further, the ultrastructure in the control and DG−/− embryoid bodies was analyzed by electron microscopy. At lower magnifications, microvilli can be seen protruding from the apical surfaces of the endodermal cells. In other sections, that tight junctions had formed between endodermal cells in both control and DG−/− embryoid bodies. This indicates that the endodermal cells are able to generate a polarized morphology in the absence of dystroglycan. In extracellular spaces beneath the endodermal cell layer in control embryoid bodies, basement membranes associated with the basal surfaces of the endodermal cells were detected. These basement membranes displayed the characteristic lamina lucida/lamina densa morphology and ran parallel with the plasma membrane maintaining a relatively uniform distance from it. In some sections, fibrillar collagen was seen making contact with the sub-endodermal basement membrane. In contrast, inspection of the DG−/− embryoid bodies revealed that the sub-endodermal basement membranes were completely absent. Instead, the endodermal cells appeared to rest upon a fibrous matrix. A similar fibrous matrix was detected underneath the basement membrane of control embryoid bodies. However, in control embryoid bodies, the basement membrane separated the endodermal plasma membrane from the fibrous matrix whereas in DG−/− mutant embryoid bodies, the endodermal plasma membrane appeared to directly connect with the fibrous matrix. Another feature of the sub-endodermal compartment in DG−/− embryoid bodies is that punctate deposits of electron-dense material that might represent aggregated basement membrane proteins were observed. No sub-endodermal basement membranes were detected in any of the DG−/− embryoid bodies examined (n=24 from independent experiments). In sum, the ultrastructural analysis revealed that DG−/− endodermal cells exhibit a polarized morphology, but do not form a basement membrane on their basal surface, in agreement with the light microscopy findings.

Dystroglycan is Required For the Formation of Laminin-1 Clusters on the Surface of Embryonic Stem Cells.

The foregoing results demonstrate that dystroglycan is required for the formation of the sub-endodermal basement membrane in embryoid bodies, and suggest that DG-laminin interactions are critical for the deposition of other basement membrane molecules. Thus, a DG-laminin complex might be involved in nucleating basement membrane assembly. An important feature of a cell surface molecule involved in the initial formation of basement membranes would seem to be that it could interact with soluble matrix molecules, before they are assembled into an insoluble structure. To investigate this idea further, the finding that dystroglycan is expressed in undifferentiated ES cells was exploited. In those cells, dystroglycan is typically localized diffusely over the surface of the cells with some apparently concentrated localization at sites of cell-cell contact. Undifferentiated ES cells express little, if any, laminin-1 and the scant amount of laminin-1 that is present in the cultures is apparently derived from spontaneously-differentiated endodermal cells that are present at low frequency. Therefore, laminin-1 was added to the ES cell cultures. Immunofluorescence staining of α-dystroglycan and LMα1 indicated that after its addition to the culture medium, laminin-1 was deposited in clusters, co-localized with dystroglycan, on the surfaces of control ES cells, but not on DG−/− ES cells. On control ES cells, these clusters formed at laminin-1 concentrations far below the critical concentration for laminin-1 self-assembly observed in vitro (~100 nM; Yurchenco et al., *J. Biol. Chem.* 260: 7636–44 (1985)), and were routinely observed at concentrations of 1 nM, the lowest concentration tested. At 7.5 nM laminin-1, only faint, punctate staining on the surface of DG−/− cells was observed. This punctate staining was dependent on the addition of laminin-1 to the culture, but the majority of it was of a fine particulate nature similar to that observed on the surface of the culture dish and may therefore represent aggregated laminin non-specifically associated with the cell surface. The formation of laminin-1 clusters was not detected on DG−/− ES cell lines at 120 nM, the highest concentration of laminin-1 tested. However, at this high concentration, large particles of laminin-1 were detected over the surfaces of the cells and on exposed regions of the culture dish in both control and DG−/− cultures.

DG−/− ES cells were tested for a general defect in extracellular matrix assembly on their surfaces by examining the status of fibronectin. Immunostaining of cells indicated that fibronectin, either from the serum in the culture medium or produced by the ES cells, was present in a fibrillar staining pattern on the dorsal surfaces of control and DG−/− ES cells. The proportion of cells displaying this pattern of staining was equivalent among the cultures suggesting that the extent of fibronectin matrix assembly is not affected in the absence of dystroglycan. Interestingly, the fibronectin staining pattern was similar, though not identical, to that of laminin-1, consistent with other reports of the co-distribution on these molecules on cell surfaces (Darribere et al., *Cell Tissue Res.* 246: 45–51 (1986); Hayman et al., *J. Cell Biol.* 88: 352–57 (1981)).

Restoration of Dystroglycan Expression Rescues Phenotypes in Dystroglycan-Null Embryonic Stem Cells and Embryoid Bodies.

The above results are consistent with the conclusion that dystroglycan is required for basement membrane formation in embryoid bodies and laminin clustering on ES cells. However, to address the possibility that the observed phenotypes were due to stable secondary changes in the DG−/− ES cell lines rather than the primary loss of dystroglycan function, the possibility that the phenotypes observed in DG−/− ES cells and embryoid bodies could be rescued by restoration of dystroglycan expression was explored.

An adenovirus carrying a rabbit dystroglycan cDNA (DG adenovirus) was used for these studies. Because adenoviruses have not been used extensively for gene transfer in ES cells or embryoid bodies, the ability of the adenoviral vector to confer lacZ reporter gene expression in these systems was tested. Sections of embryoid bodies that were infected with adenovirus containing a lacZ gene were examined for lacZ gene expression by β-galactosidase staining. This analysis revealed that nearly 100% reporter gene transfer was achieved in ES cells. There was little apparent cytotoxicity resulting from the adenovirus mediated gene transfer. In embryoid bodies, the expression was often limited to the outer endodermal layer, though not all embryoid bodies showed expression of the reporter construct. The virus may be excluded from the core of the embryoid body by the endodermal layer, or those cells might be more permissive to infection than others. This was fortuitous for the experiments because dystroglycan is normally expressed in endodermal cells.

Following the above verification, DG−/− ES cells were infected with the DG adenovirus. Western blot analysis of infected and uninfected ES cells and 10-day-old embryoid bodies indicated that infection restored dystroglycan expression in both DG−/− ES cells and embryoid bodies. After infection of DG−/− ES cells, laminin-1 was added to the culture medium and laminin clustering was assayed by immunostaining of cells and embryoid bodies. Cells expressing the viral construct were identified by staining with an anti-dystroglycan antibody. In cells now expressing dystroglycan, laminin clusters co-localized with dystroglycan. Similarly, embryoid bodies were infected with the dystroglycan adenovirus. Embryoid bodies expressing dystroglycan were identified by an immunofluorescence assay. In DG−/− embryoid bodies showing renewed dystroglycan expression in the endodermal layer, typical basement membrane co-localization of laminin-1 with dystroglycan was observed. When type IV collagen localization in DG adenovirus-infected embryoid bodies, was examined, type IV collagen, too, was seen associated with DG-expressing cells in a basement membrane staining pattern. Control experiments utilizing an adenovirus carrying a green fluorescent protein cDNA did not rescue, or alter, the mutant phenotypes observed in DG−/− ES cells and embryoid bodies.

Experimental Procedures

Virus overlay protein blot assay (VOPBA). The method of (P. Borrow and M. Oldstone, *J. Virol.* 66: 7270 (1992)) was modified as follows: A goat anti-mouse IgG antibody conjugated with horseradish peroxidase (Pierce) (1:5,000 in PBS) was used to substitute rabbit anti-mouse IgG and I125-protein A, afterward Enhanced Chemiluminescence assay was performed with the SuperSignal Chemiluminescent substrate (Pierce).

Binding of LCMV and LFV to cell membrane proteins. VOPBA was performed with either enriched uninfected BHK cell culture fluid, LCMV (strain Cl 13) or LFV on identical blots containing 50 μg of purified cell membrane proteins prepared from two cell lines susceptible to LCMV infection: monkey kidney line Vero E6 and mouse fibroblast line MC57; and two cell lines resistant to LCMV infection and binding: human T-lymphocyte line Jurkat and mouse T-lymphocyte line RMA.

Purification of the receptor protein. Monolayers of MC57 cells were dissociated with PBS/5 mM EDTA. Cells were solubilized in a buffer containing 20 mM Tris (pH 7.4), 0.15 M NaCl, 1.5% octyl-glucoside, 0.5 mM PMSF, 1× Complete™ protease inhibitor cocktail (Boehringer Mannheim) for 60 minutes on ice. The sample was then spun for 15 minutes at 2,500 g and the supernatant was centrifuged again for 60 minutes at 100,000 g at 4° C. The cleared sample was loaded onto a Mono Q HR5/5 column (Pharmacia) and eluted with 1 M NaCl. Aliquots of the protein fractions were separated on 6% SDS-PAGE for VOPBA analysis to locate the fractions enriched for LCMV-binding activity. The peak fractions were combined and passed through a 10 ml lentil-Sepharose column which did not retain the putative receptor of LCMV. Flow through material was then loaded directly onto a 10 ml wheat germ agglutinin-Sepharose column, from which the protein was eluted with 0.5 M N-acetylglucosamine. Subsequently, VOPBA positive fractions were combined and put through a 5 ml jacalin-Sepharose column. After washing with 0.2 M melibiose/1M NaCl, 3 M KSCN and 1% SDS to remove contaminating proteins, the whole column was disrupted and the Sepharose was boiled in SDS sample buffer with 2.5% β-mercaptoethanol for 5 minutes. The denatured sample was then concentrated 5-fold by UltraFree-MC centricons (MilliPore) before resolved on 6% SDS-PAGE.

Sequencing of tryptic peptides. The Coomassie blue-stained protein band with VOPBA binding activity was excised from SDS-PAGE and submitted for peptide sequencing analysis. After in-gel digestion with trypsin, the sequences of five peptides were determined at the Harvard Microchemistry Facility by collisionally activated dissociation on a Finnigan TSQ7000 Triple Quadrupole Mass Spectrometer. GT384, GT441, and GT417 were homologous to regions of Dystroglycan precursor. GT429 was homologous to aa 3–13 of jacalin, GT348 to aa 31–39 of U1 small nuclear ribonucleoprotein.

Binding of LCMV, LFV, and other arenaviruses to α-dystroglycan. Four identical blots containing purified dystroglycan proteins were used in VOPBAs with either no virus or LCMV strains Cl 13, Arm5 and WE54, arenaviruses LFV, Mobala, Oliveros and Guanarito. Each blot contained protein samples from three different sources, 10 μg of purified 156 kD α-DG protein from rabbit skeletal muscle; 40 μg of recombinant 68 kD GST-FP-D; 40 μg of recombinant 82 kD GST-FP-B.

Blocking of infection by LCMV with soluble α-dystroglycan protein. $1 \times 10^5$ of 3T6 cells were plated per well into a 24-well plate the day before the experiment. Aliquots of $1.6 \times 10^5$ pfu of LCMV strain Cl 13 and VSV Indiana strain were incubated for 20 minutes on ice with either BSA or purified α-DG protein from rabbit skeletal muscle at concentrations of 0, 9 pM, 90 pM, 0.9 nM, 9 nM and 90 nM in a final volume of 150 microliters. One aliquot of treated virus was then incubated with cells for 30 minutes at 37° C. before replaced with fresh growth medium. As a control, LCMV Cl 13 infection was also performed in the presence of increasing concentrations of bovine serum albumin (BSA). 16 hours later, samples of culture supernatant were taken for determination of virus titers by plaque assay on Vero cells. At this time, the cells were also immunostained using specific antibodies to detect LCMV nucleoprotein or VSV glycoprotein, and the number of infected cells was observed under fluorescence microscopy. Cells were fixed with acetone and analyzed by immunofluorescence staining with a mAb 1-1-3 to detect LCMV nucleoprotein or mAb I1 to detect VSV glycoprotein. A FITC-conjugated goat anti-mouse IgG antibody diluted 1:20 with PBS was used as the secondary antibody in the staining.

Results were quantitated as an average of at least 4 fluorescent areas and plotted as percentage of control where no competing protein was added.

Expression of α-dystroglycan to confer LCMV infection of DG−/− ES cells. $2 \times 10^5$ of ES cells were plated per well into a 24-well plate the day before $2 \times 10^9$ adenovirus particles carrying rabbit dystroglycan cDNA (estimated MOI of 5) was added in the culture medium. Two days later, aliquots of LCMV Cl 13 virus in 200 microliters were added to each well. Following 45 minutes' incubation at 37° C., the inoculum was replaced by 1 ml fresh ES growth medium. 16 hours later, cells were fixed with acetone and immunostained with antibody 1-1-3 to detect the LCMV nucleoprotein by immunofluorescence.

Requirement of α-DG expression for LCMV infection. Parental wt ES cells, DG null ko cells and ko cells reconstituted with dystroglycan (ko+DG) were infected with LCMV strain Cl 13 at multiplicity of infection (MOI) of 0.1, 1 and 10 respectively. 16 hours later, cells were stained with mAb 1-1-3 to detect LCMV nucleoprotein by immunofluorescence. dystroglycan reconstitution was achieved by infecting ko cells with an adenovirus vector carrying rabbit dystroglycan cDNA.

Generation of dystroglycan-null ES cells and preparation of embryoid bodies. DG-/- ES cells were isolated from two independently derived parental DG-/- ES cell clones TD354 and TD556 (Williamson et al., *Hum. Mol. Genet.* 6: 831–41 (1997)) by selection in high concentration of G418 (Mortensen et al., *Mol. Cell Biol.* 12: 2391–5 (1992)) and re-targeting with a hygromycin-selectable gene disruption construct (Mortensen et al., *Proc. Natl. Acad. Sci. USA* 88: 7036–40 (1991)). DG-/- ES cells derived from both strategies yielded similar results. For simplicity, only those derived by the first method are described here. Cells lines were first passaged twice off of feeder layers in ES growth medium (GM) [DMEM-high glucose, +20% heat-inactivated fetal bovine serum (FBS, Hyclone), 2 mM L-glutamine (Gibco/BRL), 1 mM non-essential amino acids (Gibco/BRL), $10^3$ U/ml leukemia inhibitory factor (LIF, Gibco/BRL), and 0.001% β-mercaptoethanol (Sigma, tissue culture grade)]. Selection was carries out in ES-GM+1.0 mg/ml active G418 (Gibco/BRL). After selection, surviving colonies were picked, expanded, and analyzed by Southern blotting. HindIII-digested DNA samples were screened using a HindIII-PstI fragment from intron 1 of the mouse dystroglycan gene as a probe. This screen identified one DG-/- clone from TD354 (354.B11) and one DG-/- clone from TD556 (556.E5). Most of the data presented is from 354.B11. DG+/- lines surviving selection were used as controls for subsequent experiments. For wild-type controls the parental R1 ES cells (Nagy et al., *Proc. Natl. Acad. Sci. USA* 90: 8424–8 (1993)) were passaged off of feeders. All cells lines were used for experiments between 1–7 passages after removal from the feeders. Embryoid bodies were prepared by plating $5 \times 10^5$ ES cells in 60 mm bacteriological grade plastic dishes (Fisher) in ES-GM without LIF. This medium was changed after 2d and after 4d, was replaced with DMEM +10% heat-inactivated FBS and 2 mM L-glutamine. Following, the medium was changed daily until 10d, at which time the embryoid bodies were analyzed.

Antibodies and protein analysis. The following specific primary antibodies were used: mAb 8D5 against β-DG (Novocastra), affinity purified rabbit pAb #83 against β-DG (Williamson et al., *Hum. Mol. Genet.* 6: 831–41 (1997)), mAb IIH6-C4 against α-DG (Ervasti, J. M. and Campbell, K. P., *Cell* 66: 1121–1131 (1991)), rabbit pAb #317 against the laminin α1 G domains (Durbeej et al., *Matrix Biol.* 15: 397–413 (1996)), goat pAb (1340-01) against collagen α1, 2(IV) (Southern Biotechnology Associates), rat mAb MAB1948 against perlecan (Chemicon), rabbit pAb against human fibronectin (Wennerberg et al., *J. Cell Biol.* 132: 227–38 (1996)), pAb against Pem (Lin et al., *Dev. Biol.* 166: 170–9 (1994)), mAb CH1 against cardiac tropomyosin (Lin et al., *Hybridoma* 4: 223–42 (1985)). Western blotting of embryoid body and ES cell extracts was accomplished as described (Ervasti, J. M. and Campbell, K. P., *Cell* 66: 1121–1131 (1991)) except that chemiluminescent detection of secondary antibodies was used. For immunohistochemistry of embryoid bodies, 10d cultures were collected and fixed 15–30 min in 4% paraformaldehyde, dehydrated, cleared, and embedded in paraffin. 7 μm sections were then cut on a rotary microtome, affixed the sections to slides, deparaffinized and rehydrated before staining. Hematoxylin/eosin, periodic acid-Schiff, and β-galactosidase staining was performed according to standard protocols. For immunostaining, non-specific binding was blocked with PBS +1% BSA for 1 h and the sections were incubated overnight in appropriately diluted antibody solutions. Primary antibodies were detected with fluorescently-tagged secondary antibodies (Jackson Immunoresearch). For the laminin clustering assay, ES cells were first plated onto coverslips coated with 5 μg/cm² human fibronectin (Collaborative Biomedical Products) which promoted cell spreading. After plating and overnight incubation, the culture medium was replaced with ES-GM containing varying concentrations of mouse laminin-1 (Collaborative Biomedical Products), and then incubated overnight. After incubation, coverslips were fixed in 4% paraformaldehyde in PBS for 15 min, washed and stained as described above. For all double-label immunofluorescence experiments, control experiments were performed utilizing each primary/secondary antibody combination singly, each primary antibody plus the opposite secondary antibody, and secondary antibodies alone to validate the double labeling. Sections and cells were photographed under a Nikon inverted microscope with Hoffman modulation contrast optics, a Leitz Diaplan microscope for brightfield images, or a Bio-Rad MRC 1024 laser scanning confocal microscope.

Electron Microscopy. 10d embryoid bodies were fixed with 2% paraformaldehyde/2% glutaraldehyde in PBS, rinsed three times in 0.1 M sodium cacodylate, then post-fixed with a solution of 1% $OsO_4$ and 1.25% potassium ferrocyanide in cacodylate buffer. After three rinses in cacodylate buffer, the samples were exposed to a 1% aqueous tannic acid solution for 20 min, dehydrated through a graded series of acetones, and embedded in Eponate-12 (Ted Pelling, Inc., Redding, Calif.). After embedment and polymerization, individual embryoid bodies were selected, mounted on blocks, 110 nm sections were cut using a Reichert Ultracut E ultramicrotome, and these were stained with 5% uranyl acetate followed by Reynold's lead citrate. Sections were examined and photographed with a Hitachi H-600 transmission electron microscope operated at 75 KV.

Adenoviral-mediated dystroglycan gene transfer. The DG adenovirus was constructed by sub-cloning a rabbit dystroglycan cDNA (Ibraghimova-Beskrovnaya et al., *Nature* 355: 696–702 (1992)) into the pAdRSVpA shuttle vector. The dystroglycan construct was incorporated into an adenovirus vector through standard methods of homologous recombination with Ad5 backbone dl309 by the University of Iowa Gene Transfer Vector Core. Recombinant viruses were purified using established methods (Davidson et al., *Exp. Neurol.* 125: 258–67 (1994); Graham, F. L., and Eb, A. J. v.d., *Virology* 52: 456–67 (1973)). Lysates from infected 293 cells were collected and tested for expression of dystroglycan by Western blot analysis. Recombinant virus was plaque purified, amplified, and purified by CsCl gradient centrifugation. Viruses containing lacZ and green fluorescent protein expression constructs were obtained from the University of Iowa Gene Transfer Vector Core. For infection of ES cells, $1 \times 10^9$ viral particles diluted in fresh ES growth medium was added to $1 \times 10^6$ ES cells grown under standard conditions. Estimating roughly 1% of total viral particles are infective, this corresponds to a multiplicity of infection of ~10. Cells were cultured with the virus overnight, and fresh medium was added the next day. Cells were assayed for expression of the viral construct 48–72 h after infection. For infection of embryoid bodies, $1\times10^9$ viral particles diluted in DMEM supplemented with 10% heat-inactivated FBS and 2 mM L-glutamine were added to a single 60 mm dish of 6d embryoid bodies. Fresh medium was added after overnight incubation with the virus, and the infected embryoid bodies were assayed for expression of the viral construct at 10d.

What is claimed is:

1. A method for inhibiting the binding of an arenavirus to a cellular receptor, comprising:
   a) providing, in soluble form, a reagent comprising α-dystroglycan or a portion thereof, the reagent being characterized by the ability to bind to the arenavirus thereby inhibiting the binding of the arenavirus to the cellular receptor; and b) contacting the reagent with an arenavirus particle prior to infection of a cell by the arenavirus particle.

2. The method of claim 1 wherein the arenavirus is an Old World arenavirus.

3. The method of claim 2 wherein the arenavirus is Lymphocyte Choriomeningitis Virus.

4. The method of claim 2 wherein the arenavirus is Lassa fever virus.

5. The method of claim 2 wherein the arenavirus is Mobala.

6. The method of claim 1 wherein the arenavirus is a New World arenavirus.

7. The method of claim 6 wherein the arenavirus is Oliveros.

8. The therapeutic method for treating an arenavirus infection in a patient, comprising:

a) providing a therapeutic composition comprising α-dystroglycan or a portion thereof which is characterized by the ability to bind to arenaviruses, thereby inhibiting the binding of arenaviruses to a cellular receptor; and b) administering the therapeutic composition to the patient.

9. The therapeutic method of claim 8 wherein the therapeutic composition is administered intravenously.

10. The method of claim 8 wherein the arenavirus is an Old World arenavirus.

11. The method of claim 10 wherein the arenavirus is Lymphocyte Choriomeningitis Virus.

12. The method of claim 10 wherein the arenavirus is Lassa fever virus.

13. The method of claim 10 wherein the arenavirus is Mobala.

14. The method of claim 8 wherein the arenavirus is a New World arenavirus.

15. The method of claim 14 wherein the arenavirus is Oliveros.

16. The method of claim 8 wherein the patient is human.

17. The method of claim 16 wherein the patient is a fetus.

18. The method of claim 17 wherein the therapeutic composition is administered intravenously to the mother of the fetus.

19. The method of claim 8 wherein the patient is an animal.

20. The method of claim 19 wherein the patient is a fetus.

21. The method of claim 20 wherein the therapeutic composition is administered intravenously to the mother of the fetus.

22. A method for arenavirus infection prophylaxis in an individual at risk, comprising:

a) providing a composition comprising α-dystroglycan or a portion thereof which is characterized by the ability to bind to arenaviruses, thereby inhibiting the binding of arenaviruses to a cellular receptor; and b) administering the composition to the individual at risk.

* * * * *

UNITED STATES PATENT AND TRADEMARK OFFICE
CERTIFICATE OF CORRECTION

PATENT NO. : 6,083,911
DATED : July 4, 2000
INVENTOR(S) : Campbell et al.

It is certified that error appears in the above-indentified patent and that said Letters Patent is hereby corrected as shown below: On the title page, item [73]:

Assignee, should read--Scripps Research Institute, La Jolla, California--.

Column 1, insert the following paragraph:

---This invention was made with government support under Contract No. AI09484, by the National Institutes of Health. The government has certain rights in the invention.---

Signed and Sealed this

Twenty-ninth Day of May, 2001

*Attest:*

NICHOLAS P. GODICI

*Attesting Officer*      Acting Director of the United States Patent and Trademark Office

UNITED STATES PATENT AND TRADEMARK OFFICE
CERTIFICATE OF CORRECTION

PATENT NO.    : 6,083,911
DATED         : July 4, 2000
INVENTOR(S)   : Campbell et al.

It is certified that error appears in the above-identified patent and that said Letters Patent is hereby corrected as shown below:

<u>Title page,</u>
Item [73], Assignee, add the following:
-- Scripps Research Institute, La Jolla, California. --.

<u>Column 1,</u>
Line 12, insert the following:
-- This invention was made with government support under Contract No. AI09484, by the National Institutes of Health. The government has certain rights in the invention. --.

Signed and Sealed this

Sixth Day of August, 2002

Attest:

Attesting Officer

JAMES E. ROGAN
*Director of the United States Patent and Trademark Office*